(12) United States Patent
Tsuru et al.

(10) Patent No.: US 7,998,590 B2
(45) Date of Patent: Aug. 16, 2011

(54) ADHESIVE MATERIAL

(75) Inventors: Seiichiro Tsuru, Tosu (JP); Tomoyuki Hinotani, Tosu (JP); Tetsurou Hinotani, legal representative, Saga (JP); Akiko Hinotani, legal representative, Saga (JP); Masatoshi Kita, Tosu (JP)

(73) Assignee: Hisamitsu Pharmaceutical Co., Inc., Tosu-shi, Saga (JP)

( * ) Notice: Subject to any disclaimer, the term of this patent is extended or adjusted under 35 U.S.C. 154(b) by 705 days.

(21) Appl. No.: 11/587,944

(22) PCT Filed: Apr. 27, 2005

(86) PCT No.: PCT/JP2005/008033
§ 371 (c)(1), (2), (4) Date: Oct. 27, 2006

(87) PCT Pub. No.: WO2005/105150
PCT Pub. Date: Nov. 10, 2005

(65) Prior Publication Data
US 2007/0231591 A1    Oct. 4, 2007

(30) Foreign Application Priority Data

Apr. 28, 2004 (JP) ............... P2004-133944
Apr. 28, 2004 (JP) ............... P2004-134005

(51) Int. Cl.
*A61K 47/36* (2006.01)
*A61K 47/32* (2006.01)
*A61K 9/70* (2006.01)
*A61L 15/58* (2006.01)

(52) U.S. Cl. ......... 428/497; 428/353; 428/355; 428/532

(58) Field of Classification Search ............ None
See application file for complete search history.

(56) References Cited

U.S. PATENT DOCUMENTS

| | | | | |
|---|---|---|---|---|
| 2,042,917 A | * | 6/1936 | Von Brandt | 106/38.51 |
| 3,119,697 A | * | 1/1964 | Leo et al. | 426/575 |
| 3,956,273 A | * | 5/1976 | Guiseley | 536/120 |
| 5,670,636 A | * | 9/1997 | Provonchee | 536/123.1 |
| 6,319,507 B1 | * | 11/2001 | Delrieu et al. | 424/401 |
| 7,045,137 B1 | * | 5/2006 | Muta et al. | 424/400 |
| 2003/0064104 A1 | * | 4/2003 | Stillman | 424/490 |

FOREIGN PATENT DOCUMENTS

| | | |
|---|---|---|
| CN | 1308537 A | 8/2001 |
| JP | 55-94316 A | 7/1980 |
| JP | 57-42617 A | 3/1982 |
| JP | 61-257919 A | 11/1986 |

(Continued)

OTHER PUBLICATIONS

English Translation of Japanese Pharmacopoeia Manual, "Agar", 13th Ed., pp. 242-245, 1996.

*Primary Examiner* — John J Figueroa
(74) *Attorney, Agent, or Firm* — The Nath Law Group; Susanne M. Hopkins; Ari G. Zytcer (57) ABSTRACT

An adhesive article comprising a backing and an adhesive layer disposed on at least one side of the backing, wherein the adhesive layer is formed from an adhesive base that contains substantially no gelatin and does contain readily soluble agar.

8 Claims, 1 Drawing Sheet

FOREIGN PATENT DOCUMENTS

| | | |
|---|---|---|
| JP | 64-1701 A | 1/1989 |
| JP | 02-193915 A | 7/1990 |
| JP | 2002-302437 A | 10/2002 |
| JP | 2003-169823 A | 6/2003 |
| JP | 2003-518008 A | 6/2003 |
| JP | 2003-313110 A | 11/2003 |
| WO | 99/17944 A1 | 4/1999 |
| WO | WO 0044336 A1 * | 8/2000 |
| WO | 2005/105060 A1 | 11/2005 |
| WO | 2005/105150 A1 | 11/2005 |

* cited by examiner

Fig.1

ADHESIVE MATERIAL

TECHNICAL FIELD

This invention relates to an adhesive article.

BACKGROUND ART

The adhesive layer of an adhesive article, such as a cataplasm used as a drug, or a compress used as a cosmetic or quasi-drug, contains water and, depending on the application, a medicinal component, a cosmetic component, or the like. In the past, when an adhesive layer had a high water content, an adhesive base was used that contains gelatin and/or a water-soluble polymer such as a polyacrylic acid or polyacrylate.

In particular, an adhesive base containing gelatin can form an adhesive layer that has a high water content and that has excellent shape retention and cohesion, and affords an adhesive article that leaves behind less sticky residue, has less oozing of the adhesive, and other advantages. An adhesive base has also been disclosed in which agar is added to a gelatin-based adhesive base in an effort to further improve the water content and shape retention (for example, see Patent document 1).
Patent document 1: Japanese Laid-Open Patent Application S57-42617.

DISCLOSURE OF THE INVENTION

Problems to be Solved by the Invention

However, with a conventional adhesive base containing gelatin, such as the adhesive base discussed in Patent document 1, the pH of the adhesive base sometimes limited which substances (such as medicinal components) could be added besides gelatin. This is because if the pH of the adhesive base is outside a specific pH range over which the gelatin will satisfactorily retain its shape, have cohesive strength, and so forth, there will problems in that the shape retention, cohesion, adhesion, and so forth will decrease. These problems become particularly pronounced over time. Consequently, the above-mentioned conventional adhesive bases could not be considered satisfactory because they limited the freedom of design of an adhesive article.

It is possible not to add any gelatin so that the components which can be added will not be limited by the pH of the adhesive base, but with conventional adhesive bases containing no gelatin, it was difficult to obtain an adhesive article with the high water content that was made possible by the addition of gelatin, and that had satisfactory shape retention and cohesion.

The present invention was conceived in light of the problems encountered with the above prior art, and provides an adhesive article that has a sufficiently high water content, excellent tack strength, and sufficiently reduced sticky residue, even when the blend is such that the desired components are contained and the desired pH is achieved.

Means for Solving the Problems

As a result of diligent research aimed at achieving the stated object, the inventors arrived at the present invention upon discovering that if a specific agar is contained in an adhesive base, then an adhesive layer having a high enough water content can be formed without having to add gelatin, and the adhesive layer thus formed will have excellent shape retention and adhesion, and oozing of the adhesive and sticky residue left behind after use will both be sufficiently reduced.

Specifically, the adhesive article of the present invention comprises a backing and an adhesive layer that is disposed on at least one side of the backing, wherein the adhesive layer is formed from an adhesive base that contains substantially no gelatin and does contain readily soluble agar.

The term "readily soluble agar" as used in the present invention means agar that dissolves substantially 100% at a temperature of 70° C. As long as the agar has this property, there are no particular restrictions on its composition, molecular weight, form, gel strength, sol viscosity, coagulation point, pH, water absorptivity, partability, and so forth.

The term "gel strength" as used in the present invention shall be the gel strength ($g/cm^2$) of a gel prepared from a 1.5 wt % solution of agar and coagulated by being allowed to stand 15 hours at 20° C., expressed in terms of the maximum weight (number of grams) that can be withstood for 20 seconds per square centimeter of gel area.

Also, the phrase "contains substantially no gelatin" as used in the present invention means that either no gelatin is contained, or if some is contained, the amount is small enough not to affect the gel strength of the adhesive layer formed from the adhesive base. Whether or not the gel strength of the adhesive layer is affected here can be determined by the following method. The gel strength of an adhesive layer formed from a certain adhesive base is deemed to be unaffected if the gel strength of the adhesive layer formed from this adhesive base to which a certain amount of gelatin has been added either does not increase or does not change, and a certain amount of gelatin can be considered to meet the requirement of "contains substantially no gelatin." In comparing gel strength, a difference shall only be recognized after taking measurement error into account.

With the present invention, the use of readily soluble agar makes it possible to obtain an adhesive article that has a sufficiently high water content, excellent adhesion, and sufficiently reduced sticky residue, which was achieved in the past by using gelatin alone, or gelatin and agar together. At the same time, it is possible for the adhesive article to contain the desired components and to have the desired pH.

Dissolving agar usually requires a high temperature (approximately 90° C. or higher). Therefore, if ordinary agar is used, the reaction of the crosslinking agent (a polyvalent metal salt such as an aluminum compound) contained in the adhesive base may be problematic during manufacture, such as the reaction proceeding more than necessary. With the present invention, however, a high temperature (of 90° C. or higher) is not needed to dissolve the readily soluble agar, so the above problem is sufficiently mitigated. Therefore, the adhesive article of the present invention also has the advantage of being easier to manufacture.

Further, since a high temperature (of 90° C. or higher) is not needed to dissolve the readily soluble agar with the present invention, volatile or pyrolyzable components that were lost in large quantity during manufacture with a conventional adhesive article can be efficiently added to an adhesive article. Also, there is no need for the apparatus, energy, time, and so forth that would otherwise be necessary to cool the agar solution in order to add volatile or pyrolyzable components, so the manufacturing process can be simplified.

As a result, with the present invention, both the effect of pH and the effect of heat during manufacture can be sufficiently reduced, which affords far greater freedom in the blending of the adhesive article.

Furthermore, the sagging of the adhesive layer that was seen during the use of conventional cataplasms containing gelatin can also be sufficiently reduced. The reason for this seems to be that having substantially no gelatin contained prevents the state of the gelatin from changing when the outside air temperature is high (such as 30° C. or higher), which would otherwise lead to a drop in the cohesive strength of the adhesive layer.

Also, it is preferable with the adhesive article of the present invention for the adhesive base to further contain a volatile component or pyrolyzable component.

As discussed above, an advantage to the adhesive article of the present invention is that since there is no need to cool the agar solution before mixing in a volatile component or pyrolyzable component, even when such components are added, the manufacturing process can still be simplified. Also, even if the pH of the adhesive base is adjusted in order to add a volatile component or pyrolyzable component to the adhesive article of the present invention, the adhesive layer will still have a high water content and good shape retention, cohesion, and adhesion. Accordingly, an adhesive article containing volatile components or pyrolyzable components in the desired blend proportions can be obtained more easily than in the past.

Also, with the adhesive article of the present invention, the adhesive base preferably contains a polyacrylic acid and/or a salt thereof.

If the adhesive base contains a polyacrylic acid and/or a salt thereof, the adhesive layer that is formed will have better shape retention and adhesion.

In this case, the amount in which the polyacrylic acid and/or salt thereof is contained is preferably adjusted to between 5 and 25 weight parts per weight part of the readily soluble agar. The polyacrylic acid and/or salt thereof is preferably contained in the adhesive base in an amount of 4 to 8 wt %.

This allows the water content, shape retention, cohesion, and adhesion of the adhesive article to be even better.

Also, from the standpoint of increasing the tack strength in the adhesive article of the present invention, the adhesive base preferably further contains a polyvinyl alcohol.

From the standpoint of shortening the time it takes to form the adhesive layer in the adhesive article of the present invention, the adhesive base preferably further contains a polyvinylpyrrolidone or xanthan gum. With an adhesive article such as this, the time it takes until shipment as a finished product (lead time) can be shortened and productivity can be enhanced.

It is also preferable in the present invention if the readily soluble agar has a gel strength of 450 to 1000 g/cm$^2$.

If the gel strength of the readily soluble agar is less than 450 g/cm$^2$, there will be a decrease in the shape retention of the adhesive layer that is formed, the adhesive will tend migrate to the backing and ooze out from the backing, or the adhesive layer will tend to leave behind a sticky residue. On the other hand, if the gel strength is over 1000 g/cm$^2$, there will be a tendency for the cohesive strength to increase and the tack strength of the adhesive layer to be inadequate. If the readily soluble agar content is lowered in an effort to mitigate these tendencies, and the gelling ability is diminished, the material will tend not to gel, or the amount of water that the adhesive layer can contain will tend to decrease.

In another aspect of the adhesive article of the present invention, the adhesive base contains substantially no gelatin and does contain readily soluble agar, has a water content of at least 50 wt %, contains a water-soluble polymer in an amount of 3.0 to 10 wt %, and contains xanthan gum and/or a polyvinylpyrrolidone in a combined amount of from 0.01 to 1.4 wt %. This makes it possible to sufficiently reduce the oozing of water and to obtain an adhesive article having an adhesive layer that has adequate tack strength while also having an improved usage feel.

If the proportional water content in the adhesive base is less than 50 wt %, it will tend to be more difficult to form an adhesive layer with a moist feel, a cool feel, and so forth, for example. If the proportional content of the water-soluble polymer is less than 3.0 wt %, then when the water content of the adhesive base is 50 wt % or higher, there will be a tendency for the adhesive layer that is formed to have inadequate strength and shape retention, and for it to be difficult to sufficiently reduce the oozing of water from the adhesive layer. On the other hand, if the proportional content of the water-soluble polymer is over 10 wt %, there will be a tendency for the adhesive layer that is formed to be too hard, making it difficult to obtain adequate tack strength. If the proportional content of the xanthan gum and/or polyvinylpyrrolidone is less than a combined 0.01 wt %, it will tend to be difficult to obtain sufficient tack strength in the adhesive layer that is formed, but if the amount is over 1.4 wt %, the resulting adhesive layer will tend to be sticky, so its usage feel will suffer.

It is generally believed that if an ointment base having a water content of 50 wt % or higher is solidified in the form of a sheet, there will tend to be problems such as inadequate shape retention or a decrease in shape retention over time, and that it will be difficult to adequate suppress the oozing of water from the formed adhesive layer and to attain good adhesion and usage feel. However, because the above-mentioned adhesive article is equipped with an adhesive layer formed from an adhesive base that contains substantially no gelatin but does contain readily soluble agar, has a water content of at least 50 wt %, contains a water-soluble polymer in an amount of 3.0 to 10 wt %, and contains xanthan gum and/or a polyvinylpyrrolidone in a combined amount of 0.01 to 1.4 wt %, the oozing of water is sufficiently suppressed, excellent adhesion is obtained, and a good usage feel is achieved. Satisfying all of these characteristics at the same time solves the problems associated with moisture retention and safety in applications such as an adhesive article used on the face.

Furthermore, because the above-mentioned adhesive article includes an adhesive base that satisfies the above conditions, it has the advantage of taking less time to manufacture than in the past.

To allow the adhesive article to be used as a finished product, the water-soluble polymer in the adhesive layer must be crosslinked. Specifically, it takes a certain amount of time from the coating of the backing with the adhesive base until the water-soluble polymer is adequately crosslinked. This time is usually from 13 to 18 days at room temperature with an adhesive article equipped with a conventional adhesive layer in which gelatin, polyacrylic acid, or the like is used. However, an adhesive base that contains substantially no gelatin and does contain readily soluble agar, has a water content of at least 50 wt %, contains a water-soluble polymer in an amount of 3.0 to 10 wt %, and contains xanthan gum and/or a polyvinylpyrrolidone in a combined amount of from 0.01 to 1.4 wt % can form an adhesive layer in less time than in the past. Therefore, because the adhesive article of the present invention is equipped with an adhesive layer formed from such an adhesive base, the time it takes until shipment as a finished product (lead time) is shorter than with an adhesive article equipped with a conventional adhesive layer, and this improves productivity.

It is also preferable in the present invention if the above-mentioned adhesive article is a water-based adhesive article.

The term "water-based adhesive article" as used in the present invention means that the adhesive layer contains water, and refers to a medicinal or similar cataplasm, a cooling sheet, a cosmetic or similar compress, or the like. There are no particular restrictions on the structure of the water-based adhesive article, but an example is a water-based adhesive article that comprises a backing and an adhesive layer disposed on at least one face of the backing.

Even when the above-mentioned water-based adhesive article contains the desired components and has the desired pH, it can still contain enough water, have excellent tack strength, and leave behind sufficiently less sticky residue.

Also, the adhesive article of the present invention preferably has an adhesive layer that is from 0.6 to 2.0 mm thick. Using this layer thickness affords even better usage feel because the adhesive layer contains enough water while conforming to the irregular shape of the body.

The adhesive article of the present invention is favorably used as an adhesive article that is cut into a specific design. Even when the adhesive article of the present invention is cut into a specific design, there is oozing of the adhesive layer containing plenty of water from the adhesive article, so the adhesive article retains its form over a longer period, and the adhesive layer can be affixed to the required part of the body.

Effect of the Invention

With the present invention, even when the adhesive article contains the desired components and has the desired pH, it can still contain enough water, have excellent tack strength, and leave behind sufficiently less sticky residue.

BEST MODE FOR CARRYING OUT THE INVENTION

Preferred embodiments of the present invention will now be described in detail through reference to the drawings.

Figure 1:
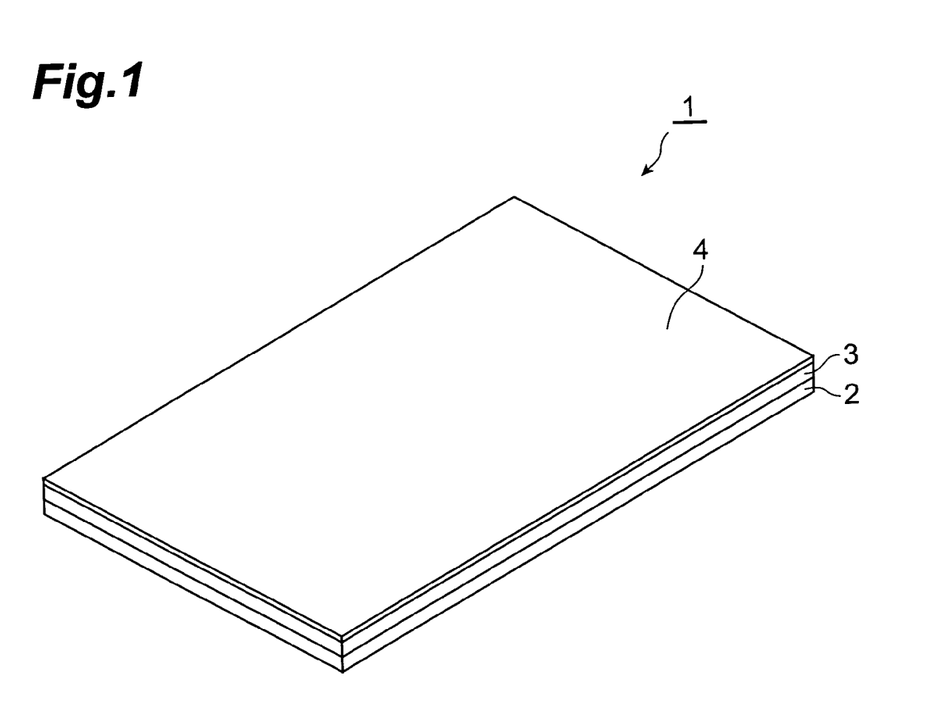
[FIG. 1] is an oblique view of a preferred embodiment of the adhesive article of the present invention.

FIG. 1 is an oblique view of a preferred embodiment of the adhesive article of the present invention. In FIG. 1, an adhesive article 1 comprises a backing 2, an adhesive layer 3 laminated over the backing 2, and a release sheet 4 affixed over the adhesive layer 3.

The adhesive layer 3 provided to the adhesive article 1 in this embodiment is formed from an adhesive base that contains substantially no gelatin, but does contain readily soluble agar.

Even when this adhesive article contains the desired components (and particularly volatile components or pyrolyzable components) and has the desired pH (and particularly a pH of 4 to 7), it will still contain enough water, have excellent tack strength, and leave behind sufficiently less sticky residue.

The readily soluble agar used in this embodiment is preferably an agar with a gel strength of 450 to 1000 $g/cm^2$, with 500 to 900 $g/cm^2$ being even better, and 600 to 800 $g/cm^2$ being particularly good. If the gel strength of the readily soluble agar is less than 450 $g/cm^2$, there will be a decrease in the shape retention of the adhesive layer 3 that is formed, and the adhesive layer 3 will migrate to the backing 2 and ooze out from the backing 2, or there will tend to be sticky residue from the adhesive layer 3. On the other hand, if the gel strength is over 1000 $g/cm^2$, there will tend to be an increase in cohesive strength and inadequate tack strength of the adhesive layer 3.

If the amount in which the readily soluble agar is added is reduced in an effort to mitigate these tendencies, and the gelling ability is diminished, the material will tend not to gel, or the amount of water. that the adhesive layer 3 can contain will tend to decrease.

Also, the readily soluble agar is preferably an agar that contains substantially no agaropectin. Agaropectin contains numerous ionic functional groups, and has almost no gelling ability. Consequently, readily soluble agar containing substantially no agaropectin is preferable because gelling can be accomplished efficiently with a smaller added amount, and dissolution is also easier.

Any known type of readily soluble agar can be used in this embodiment, but examples of commercially available types include UP-37K made by Ina Food Industry (gel strength 700 $g/cm^2$), UP-26K made by Ina Food Industry (gel strength 650 $g/cm^2$), UP-16K made by Ina Food Industry (gel strength 600 $g/cm^2$), UZ-5K made by Ina Food Industry (gel strength 420 $g/cm^2$), and UM-11K made by Ina Food Industry (gel strength 1000 $g/cm^2$).

The amount in which the readily soluble agar is added is preferably from 0.1 to 5.0 wt %, and more preferably 0.3 to 2.5 wt %, in the adhesive base. If the readily soluble agar is added in a proportion of less than 0.1 wt %, gelling will tend not to occur, but if 5.0 wt % is exceeded, adhesion will tend to decrease.

In addition to the above-mentioned readily soluble agar, the adhesive base used in this embodiment may also contain medicinal components, cosmetic components, and any components commonly added to an adhesive layer. In this embodiment, the above components can be made to be contained in the adhesive layer 3 by adding these components to the adhesive base. Examples of components that are commonly added to the adhesive layer include water-soluble polymers, water, polyhydric alcohols, polyvalent metal salts, and surfactants.

There are no particular restrictions on the medicinal components or cosmetic components, which can be suitably selected as dictated by the intended application of the adhesive article. In this embodiment, volatile components and pyrolyzable components are used as medicinal components or cosmetic components. Usually, when an adhesive base is prepared by adding a conventional agar, the agar has to be kept at a high temperature (about 90° C. or higher) to fully dissolve it. Consequently, when agar was used together with volatile or pyrolyzable medicinal components or cosmetic components that were susceptible to heat, there was pronounced loss of these components. However, with the present embodiment in which the above-mentioned readily soluble agar is used, volatile components or pyrolyzable components can be used at the same time, and an adhesive article with higher commercial value can be easily obtained. Also, since these components can be added directly to an adhesive base containing agar, another advantage is that the manufacturing process can be simplified.

The volatile component may be one that volatilizes when subjected to heat (such as heat produced during manufacture), examples of which include eucalyptus oil, nutmeg oil, thyme oil, mint oil, menthol, camphor, pinene, borneol, limonene, and other such terpenes; lavender, peppermint, Japanese mint, geranium, lime, chamomile, and other such herbal extracts; ethyl alcohol, isopropyl alcohol, and other such lower alcohols; fragrances, flavorings, and other such flavoring agents; amyl nitrite, trimethadione, and other such drugs and cosmetics; isostearic acid, octanoic acid, oleic acid, and other such $C_8$ to $C_{22}$ fatty acids; oleyl alcohol, lauryl alcohol, and other such $C_8$ to $C_{22}$ fatty acid alcohols; ethyl oleate, isopropyl myristate, butyl stearate, methyl laurate, and other such lower alkyl esters of $C_8$ to $C_{22}$ fatty acids; diisopropyl adipate and other such dialkyl esters of $C_6$ to $C_8$ diacids; glyceryl monolaurate and other such $C_8$ to $C_{22}$ fatty acid monoglycerides; and liquid excipients composed of tetrahydrofurfuryl alcohol polyethylene glycol ether, polyethylene glycol, propylene glycol, 2-(2-ethoxyethoxy)ethanol, diethylene glycol monomethyl ether, and mixtures of these.

When menthol is used, for instance, the amount in which it is contained in the adhesive base is preferably from 0.005 to 5.0 wt %, and even more preferably 0.01 to 2.0 wt %. The medicinal effect of the menthol will tend not to be obtained if the menthol content is less than 0.005 wt %, but the menthol will tend to ooze out of the adhesive layer if the content is over 5.0 wt %.

Any pyrolyzable component may be used as long as it is a substance that is unstable with respect to heat (such as heat produced during manufacture), examples of which include diclofenac, felbinac, indomethacin, ketoprofen, and other such non-steroidal anti-inflammatory drugs having carboxylic acid groups; prostaglandins, albumin, and other such proteins; diphtheria toxin and other such toxins; catalase and other such enzymes; cyclosporin A, hirudin, somatostatin, timopentin, and other such peptides; estrogen and other such hormones; human growth hormone, porcine growth hormone, bovine growth hormone, human calcitonin, salmon calcitonin, carbocalcitonin, insulin, and other such peptide hormones; hormone antagonists; acetylcholine and other such neurotransmitters; neurotransmitter antagonists; hyaluronic acid and other such glycoproteins; alpha-lipoprotein and other such lipoproteins; IgG and other such immunoglobulins; interferon, interleukin, and other such immunomodulators; estrogen receptor protein and other such cellular receptors; glycosaminoglycanes such as non-fractionated heparins, heparins of low molecular weight, chondroitin-4-sulfate, chondroitin-6-sulfate, and derivatives of these; prostaglandin; Korean ginseng, amica, Calendula officinalis, and other such herbal extracts; selenium yeast, beer yeast, and other types of yeast; ovalbumin, gelatin, and other such animal proteins; gluten and other such vegetable proteins; hydrolyzed collagen, hydrolyzed wheat gluten, and other such hydrolyzed animal or vegetable proteins; hyaluronic acid and other such natural polysaccharides; lecithin, collagen, placenta extract, ascorbic acid and esters thereof, retinol and esters thereof, vitamin A oil, hydroxocobalamin acetate, ergocalciphenol, and other such vitamins; isosorbide nitrate, nitroglycerine, testosterone enanthate, ergotamine tartrate, pergolide, nicotine, aluminum nitrite, ethchlorvynol, paramethadione, and scopolamine.

When ketoprofen is used, for instance, the amount in which it is contained in the adhesive base is preferably from 0.01 to 5.0 wt %, and even more preferably 0.1 to 1.0 wt %. A medicinal effect will tend not to be obtained if the ketoprofen content is less than 0.01 wt %, but if the content is over 5.0 wt % the amount will tend to be excessive with respect to the required effect.

Examples of other components having a medicinal effect besides the above-mentioned volatile components and pyrolyzable components include flurbiprofen, suprofen, loxoprofen, piroxicam, methyl salicylate, glycol salicylate, and other such non-steroidal anti-inflammatory drugs; hydrocortisone, dexamethasone, fluocinolone acetonide, fludroxycortide, beta-methasone valerate, clobetasone butyrate, clobetasol propionate, and other such steroidal anti-inflammatory drugs; pepper extract, nonylic vanillylamide, and other such heat-sensitive substances; and diphenhydramine hydrochloride, chlorpheniramine maleate, and other such antihistamines.

When beta-methasone valerate is used, for instance, the amount in which it is contained in the adhesive base is preferably from 0.001 to 0.5 wt %, and even more preferably 0.005 to 0.2 wt %. A medicinal effect will tend not to be obtained if the beta-methasone valerate content is less than 0.001 wt %, but if the content is over 0.5 wt % side effects will tend to be more severe.

Examples of water-soluble polymers include polyacrylic acids, polyacrylates, and water-soluble polymers other than polyacrylic acids and there salts, such as polyvinyl alcohol, polyvinylpyrrolidone, methoxyethylene-maleic anhydride copolymer, methacrylic acid copolymer, polysaccharide-based sodium alginate, ammonium alginate, carboxymethyl cellulose, carboxymethyl cellulose sodium, hydroxymethyl cellulose, hydroxypropyl cellulose, hydroxypropyl ethyl cellulose, methyl cellulose, soluble starch, carboxymethyl amylose, dextrin, gum arabic, tragacanth gum, and xanthan gum. Other examples include agar, agarose, carrageenan, guar gum, locust bean gum, pectin, starch, beta glucan, pullulan, casein, ethyl cellulose, hydroxyethyl cellulose, nitrocellulose, cationic cellulose, sodium polyacrylate, carboxyvinyl polymer, polyacrylamide, polyacrylamide-acrylate copolymer, polyvinylpyrrolidone-vinyl alcohol copolymer, polyvinyl ether, isobutylene-maleic anhydride copolymer, N-vinylacetamide, a copolymer of N-vinylacetamide and acrylic acid and/or an acrylate, and polyethylene oxide. These water-soluble polymers can function as the base for the adhesive layer 3. Also, the above water-soluble polymers can be used singly or in combinations of two or more types.

The amount in which the water-soluble polymer is contained in the adhesive base is preferably from 1 to 25 wt %, and even more preferably 5 to 10 wt %. If the water-soluble polymer content is less than 1 wt %, sticky residue and oozing will be more apt to occur, but if 25 wt % is exceeded, the material will tend to be difficult to work with or tack strength will decrease.

Of the above-mentioned water-soluble polymers, the adhesive base used in this embodiment preferably contains a polyacrylic acid and/or a salt thereof. This affords better shape retention and adhesion of the adhesive layer 3 that is formed.

In this case, the amount in which the polyacrylic acid and/or salt thereof is added is preferably adjusted to be from 5 to 25 weight parts per weight part of readily soluble agar. Also, the polyacrylic acid and/or salt thereof is preferably contained in an amount of 4 to 8 wt % in the adhesive base. This allows the adhesive article to have an even higher water content and better shape retention, cohesiveness, and adhesion. If the polyacrylic acid and/or salt thereof is contained in an amount less than 5 weight parts per weight part of the readily soluble agar, there will be a tendency for the tack strength to be too high or the adhesive layer to be hard and brittle, but if the amount is over 25 weight parts per weight part of the readily soluble agar, there will be a tendency for shape retention to decrease and the tack strength to be inadequate.

From the standpoint of increasing tack strength, of the above-mentioned water-soluble polymers, the adhesive base used in this embodiment preferably contains a polyvinyl alcohol.

Further, from the standpoint of increasing tack strength, of the above-mentioned water-soluble polymers, the adhesive base used in this embodiment preferably contains a polyacrylic acid and/or a salt thereof.

From the standpoint of shortening the time it takes to form the adhesive layer, the adhesive base preferably further contains a polyvinylpyrrolidone or xanthan gum. This shortens the time it takes until shipment as a finished product (lead time) and boosts the productivity of the adhesive article.

The water used here can be purified water, sterilized water, natural water, or the like. This water serves to disperse or dissolve the readily soluble agar, water-soluble polymer, and other components. Furthermore, the water itself has the effect of markedly improving the feel of the product during and after its use.

The amount in which the water is contained in the adhesive base is preferably from 30 to 95 wt %, and even more preferably 45 to 65 wt %. The material will tend to be more difficult to work with and more costly if the amount added is less than 30 wt %, but if 95 wt % is exceeded it will tend to be difficult to maintain good shape retention.

Examples of polyhydric alcohol include glycerin, polyethylene glycol, 1,3-butylene glycol, propylene glycol, dipropylene glycol, sorbitol, and xylytol. Of these, glycerin is particularly favorable because it is easy to work with, has a good usage feel, and so on.

The amount in which the polyhydric alcohol is contained in the adhesive base is preferably from 10 to 60 wt %, and even more preferably 20 to 40 wt %. The water will tend to volatilize out of the preparation during application, reducing tack strength and making the adhesive article more apt to coming off if the amount added is less than 10 wt %, but there will be a tendency for the tack strength to be too low if 60 wt % is exceeded.

Examples of polyvalent metal salts include aluminum hydroxide, aluminum hydroxide gel, hydrous aluminum silicate, synthetic aluminum silicate, kaolin, aluminum acetate, aluminum lactate, aluminum stearate, calcium chloride, magnesium chloride, aluminum chloride, dihydroxyaluminum aminoacetate, magnesium metasilicate aluminate, and magnesium silicate aluminate. Of these, it is particularly favorable to use dihydroxyaluminum aminoacetate, synthetic aluminum silicate, or magnesium metasilicate aluminate.

The amount in which the polyvalent metal salt is contained in the adhesive base is preferably from 0.01 to 1 wt %, and even more preferably 0.02 to 0.5 wt %. If the added amount is less than 0.01 wt %, there will be a tendency for the reaction not to proceed enough, resulting in inadequate strength, but if 1 wt % is exceeded, there will be a tendency for the reaction to proceed too quickly during manufacture, resulting in uneven gelling, which makes the material more difficult to work with and leads to even adhesion of the ointment.

Examples of surfactants include sodium dioctylsulfosuccinate, alkyl sulfates, sodium 2-ethylhexylalkylsulfates, sodium n-dodecylbenzenesulfonates, and other such anionic surfactants; hexadecyltrimethylammonium chloride, octadecyldimethylbenzylammonium chloride, polyoxyethylene dodecylmonomethylammonium chloride, and other such cationic surfactants; and polyoxyethylene stearyl ether, polyoxyethylene hydrogenated castor oil, polyoxyethylene tridecyl ether, polyoxyethylene nonylphenyl ether, polyoxyethylene octylphenyl ether, polyethylene glycol monostearate and other such polyoxyethylene monostearates, sorbitan monostearate, sorbitan monopalmitate, sorbitan sesquioleate, polyoxyethylene sorbitan monolaurate, polyoxyethylene sorbitan monooleate, glycerol monostearate, polyglycerol fatty acid ester, polyoxyethylene octadecylamine, and other such nonionic surfactants. Of these, it is particularly favorable to use polyethylene glycol monostearate, polyoxyethylene hydrogenated castor oil, or polyoxyethylene sorbitan monooleate.

The amount in which the surfactant is contained in the adhesive base is preferably from 0.01 to 5 wt %, and even more preferably 0.1 to 2 wt %. Bleed-out will tend to occur if the added amount is less than 0.01 wt %, but if 5 wt % is exceeded, it will tend to be difficult to maintain good shape retention.

The adhesive base used in this embodiment can further contain, as needed, skincare components, moisturizing components, antioxidants, crosslinking agents, preservatives, tackifiers, dissolution agents, colorants, perfumes, UV absorbents, inorganic fillers, pH regulators, and so forth.

Examples of skincare components include aloe extract, rose fruit extract, orange extract, raspberry extract, kiwi extract, cucumber extract, gardenia extract, chamomile extract, hawthorn extract, juniper extract, jujube extract, duke extract, tomato extract, loofah extract, succinyl kefiran, maleyl kefiran, malt root extract, rose extract, collagen, ceramide, squalane, hyaluronic acid, allantoin, horse chestnut extract, water-soluble placenta extract, vitamin A, vitamins B, vitamin C, vitamin D, vitamin E, and derivatives of these.

Examples of other components besides those listed above include moutan bark, kudzu root, Chinese peony, Japanese angelica root, cnidium rhizome, clove, Swertia, "Soujuu", Aurantii nobilis pericarpium, Atractylodis rhizoma, bitter orange peel, cinnamon, Coptidis rhizoma, Phellodendri cortex, Ginkgo biloba, and other such herbal medicinal components; and bentonite, montmorillonite, saponite, hectorite, and other such mud components.

Examples of moisturizing components include an acylated kefiran aqueous solution, malt extract, and glycols. These can be used singly or in combinations of two or more types.

Examples of antioxidants include ascorbic acid, propyl gallate, butylhydroxyanisol, dibutylhydroxytoluene, nordihydroguaretic acid, tocopherol, tocopherol acetate, natural vitamin E, sodium nitrite, and sodium hydrogen nitrite.

Examples of crosslinking agents include slightly water-soluble aluminum compounds, polyfunctional epoxy compounds, amino resins, phenol resins, epoxy resins, alkyd resins, unsaturated polyesters, and other such thermosetting resins, isocyanate compounds, block isocyanate compounds, organic crosslinking agents, and metals or metal compounds and other such inorganic cross linking agents. These can be used singly or in combinations of two or more types.

Examples of preservatives include ethyl p-hydroxybenzoate, propyl p-hydroxybenzoate, butyl p-hydroxybenzoate, sorbic acid, and dehydroacetic acid.

Examples of tackifiers include casein, pullulan, dextran, sodium alginate, soluble starch, carboxy starch, dextrin, carboxymethyl cellulose, sodium carboxymethyl cellulose, methyl cellulose, ethyl cellulose, hydroxyethyl cellulose, polyvinyl alcohol, polyethylene oxide, polyacrylamide, polyacrylic acid, polyvinylpyrrolidone, carboxyvinyl polymer, polyvinyl ether, polymaleic acid copolymer, methoxyethylene-maleic anhydride copolymer, isobutylene-maleic anhydride copolymer, polyethyleneimine, partially saponified polyvinyl alcohol, hydoxypropylmethyl cellulose, xanthan gum, and N-vinylacetamide.

Examples of dissolution agents include diethyl sebacate, N-methyl-2-pyrrolidone, methyl salicylate, glycol salicylate, triacetin, oleyl alcohol, benzyl alcohol, isopropyl myristate, diisopropyl adipate, crotamitone, peppermint oil, camellia oil, castor oil, and olive oil.

Examples of colorants include Red No. 2 (Amaranth), Red No. 3 (Erythrosine), Red No. 102 (New Coccine), Red No. 104-1 (Phloxine B), Red No. 105-1 (Rose Bengal), Red No. 106 (Acid Red), Yellow No. 4 (Tartrazine), Yellow No. 5 (Sunset Yellow FCF), Green No. 3 (Fast Green FCF), Blue No. 1 (Brilliant Blue FCF), and Blue No. 2 (Indigo Carmine).

Examples of perfumes include peppermint oil, cinnamon oil, clove oil, fennel oil, castor oil, turpentine oil, eucalyptus oil, orange oil, lavender oil, lemon oil, rose oil, lemongrass oil, and so forth, as well as rosemary, sage, and other such plant extracts.

Examples of UV absorbents include p-aminobenzoic acid, p-aminobenzoic esters, amyl p-dimethylaminobenzoate, salicylic esters, menthyl anthranilate, umbelliferone, esculin, benzyl cinnamate, cinoxate, guaiazulene, urocanic acid, 2-(2-hydroxy-5-methylphenyl)benzotriazole, 4-methoxybenzophenone, 2-hydroxy-4-methoxybenzophenone, dioxybenzone, octabenzone, dihydroxydimethoxybenzophenone, sulisobenzone, benzoresorcinol, octyldimethyl p-aminobenzoate, ethylhexyl p-methoxycinnamate, and butylmethoxydibenzoylmethane.

Examples of inorganic fillers include calcium carbonate, magnesium carbonate, silicates (such as aluminum silicate and magnesium silicate), silicic acid, barium sulfate, calcium sulfate, calcium zincate, zinc oxide, and titanium oxide.

Examples of pH regulators include acetic acid, formic acid, lactic acid, tartaric acid, oxalic acid, benzoic acid, glycolic acid, malic acid, citric acid, hydrochloric acid, nitric acid, sulfuric acid, sodium hydroxide, potassium hydroxide, methylamine, ethylamine, propylamine, dimethylamine, diethylamine, dipropylamine, trimethylamine, triethylamine, tripropylamine, monomethanolamine, monoethanolamine, monopropanolamine, dimethanolamine, diethanolamine, dipropanolamine, trimethanolamine, triethanolamine, tripropanolamine, citrate buffer, phosphate buffer, glycine buffer, acetate buffer, and other buffers.

The adhesive base used in this embodiment can be used in a form in which, for example, it contains substantially no gelatin, but does contain readily soluble agar, has a water content of at least 50 wt %, contains a water-soluble polymer in an amount of 3.0 to 10 wt %, and contains xanthan gum and/or polyvinylpyrrolidone in an amount of 0.01 to 1.4 wt %. The result is that the oozing of water from the ointment is sufficiently reduced, and the adhesive article has adequate tack strength, while having an even better usage feel.

If the water content is less than 50 wt %, it will tend to be more difficult to obtain a sufficiently moist feel. It is even better for the water content of the adhesive base to be from 50 to 85 wt %. Setting the water content within this range makes it possible to obtain good shape retention while at the same time obtaining a good usage feel, such as a cooling feel and a bracing feel.

Also, if the proportional content of the water-soluble polymer is less than 3.0 wt %, then when the water content is 50 wt % or higher, there will be a tendency for the adhesive layer that is formed to have inadequate strength and shape retention, and for it to be difficult to sufficiently reduce the oozing of water from the ointment. On the other hand, if the proportional content of the water-soluble polymer is over 10 wt %, there will be a tendency for the adhesive layer that is formed to be too hard, making it difficult to obtain adequate tack strength.

If the proportional content of the xanthan gum and/or polyvinylpyrrolidone is less than a combined 0.01 wt %, it will tend to be difficult to obtain sufficient tack strength in the adhesive layer that is formed, but if the amount is over 1.4 wt %, the resulting adhesive layer will tend to be sticky, so its usage feel will suffer.

The adhesive layer 3 formed from an adhesive base containing the above components is disposed over the backing 2. The thickness of the adhesive layer 3 can be suitably adjusted as dictated by the intended application of the adhesive article, but from the standpoint of keeping water content, shape retention, cohesiveness, and adhesion all at a high level, a range of 0.6 to 2.0 mm is preferable.

When the adhesive article 1 is used as a facial adhesive article, for example, the thickness of the adhesive layer 3 is preferably from 0.8 to 1.6 mm. Setting the thickness to this range allows the adhesive layer 3 to contain enough water while also allowing the adhesive article to conform very well to the irregularities of the face, which enhances its moist feel and other aspects of usage feel.

There are no particular restrictions on the backing 2 used for the adhesive article 1 in this embodiment, as long as it is capable of supporting the adhesive layer 3, and the backing can be either stretchable or non-stretchable.

Specific examples of the backing 2 include woven and nonwoven fiber sheets made of polyurethane, polyester, polypropylene, polyvinyl acetate, polyvinylidene chloride, polyethylene, polyethylene terephthalate, and aluminum sheets, or made from synthetic or natural fibers such as nylon, acrylic, cotton, rayon, or acetate, as well as fiber sheets composed of a composite material of the above and a film that is permeable to water vapor.

Of these, woven and nonwoven fiber sheets made of polyester, polyethylene, and polyethylene terephthalate are preferable in terms of safety, versatility, and stretchability, and nonwoven fiber sheets made of polyethylene terephthalate are especially favorable. Even when these fiber sheets are fairly thick, they are still pliant, conform well to the skin, and do not irritate the skin very much. Furthermore, using such a fiber sheet makes it possible to obtain an adhesive article having good self-supportability.

The adhesive article 1 is also equipped with the release sheet 4 that is affixed over the adhesive layer 3. Examples of this release sheet 4 include films such as polyethylene terephthalate and other polyesters, polyvinyl chlorides, and polyvinylidene chlorides, and laminate films of wood-free paper and a polyolefin. This release sheet is preferably subjected to a silicone treatment on the side in contact with the adhesive layer 3, as this makes the product easier to work with when the release sheet 4 is peeled off from the adhesive article 1.

The method for manufacturing the adhesive article 1 of this embodiment will now be described.

First, the adhesive base is prepared. The various components such as readily soluble agar and medicinal components are added to purified water with a temperature of 65 to 85° C., and preferably 65 to 75° C., and this mixture is stirred for 5 to 15 minutes until the agar is thoroughly dissolved, which gives an adhesive base.

Next, the backing is coated with the adhesive base obtained above, and a release sheet is applied over the resulting coating. This is stored for a few days at room temperature until it is thoroughly crosslinked, thereby forming an adhesive layer.

After the adhesive layer has been formed, the product is cut into the desired shape to obtain an adhesive article.

Since this manufacturing method does not require that the readily soluble agar be dissolved at a high temperature (90° C. or higher), volatile or pyrolyzable components that underwent considerable loss during the manufacture of a conventional adhesive article can be added more efficiently to the adhesive article. Also, there is no need for the apparatus, energy, time, and so forth that would otherwise be necessary to cool the agar solution in order to add volatile or pyrolyzable components, so the manufacturing process can be simplified. Furthermore, the evaporation of not only volatile or pyrolyzable components, but also that of water can be sufficiently suppressed, the various components will end up being contained in the adhesive layer in amounts within the desired ranges, so a high-quality adhesive article can be obtained more stably.

A preferred embodiment of the present invention, and a method for manufacturing the adhesive article of the present invention, were described above, but the present invention is not limited to the above-mentioned embodiment.

For example, the shape of the adhesive article may be circular, elliptical, or some other shape. Also, holes, slits, or the like may be made in the adhesive article. Further, the When this adhesive base was scooped out with a metal spatula and examined visually, it was found that the readily soluble agar had thoroughly dissolved. Table 1 shows the various components and their blend proportions in the adhesive base thus prepared. The numerical values in Table 1 indicate weight percentages. The pH of the adhesive base was approximately 5 to 5.4.

TABLE 1

|  | Example 1 | Example 2 | Example 3 | Example 4 | Example 5 | Example 6 |
|---|---|---|---|---|---|---|
| Readily soluble agar (700 g/cm$^2$) | 0.50 | 1.00 | 0.30 | 0.50 | 1.00 | 0.50 |
| Readily soluble agar (600 g/cm$^2$) | | | | | | |
| Readily soluble agar (400 g/cm$^2$) | | | | | | |
| Readily soluble agar (1000 g/cm$^2$) | | | | | | |
| Ordinary agar | | | | | | |
| Sodium polyacrylate | 5.00 | 5.00 | 5.00 | 4.00 | 4.00 | 6.00 |
| Polyacrylic acid | 3.00 | 3.00 | 2.00 | 2.00 | 2.00 | 1.00 |
| Polyvinyl alcohol | | 1.00 | 2.00 | 2.00 | | |
| Polyvinylpyrrolidone | | | | | | |
| Glycerol | 30.00 | 10.00 | 30.00 | 20.00 | 25.00 | |
| Polyethylene glycol | | 15.00 | | | | 20.00 |
| Sorbitol | | | | 10.00 | | |
| Surfactant | 0.50 | 0.50 | 0.50 | 0.50 | 0.50 | 0.20 |
| Titanium oxide | | | 1.00 | 1.00 | 1.00 | |
| Synthetic aluminum silicate | | 0.50 | 0.50 | 1.00 | | 4.00 |
| Magnesium metasilicate aluminate | 0.30 | 0.50 | 0.30 | 0.35 | 0.40 | 0.50 |
| Edetic acid | 0.30 | 0.40 | 0.30 | 0.30 | 0.35 | 0.40 |
| Tartaric acid | 0.20 | 0.20 | 0.10 | 0.20 | 0.15 | 0.20 |
| Methylparaben | 0.20 | 0.20 | | | 0.20 | 0.20 |
| Crotamitone | 0.50 | | 0.50 | 0.50 | | |
| Menthol | 1.00 | 0.50 | 0.50 | 1.50 | 1.00 | 1.00 |
| Camphor | | 0.50 | | | 0.50 | |
| Isopropanol | | 0.50 | | | | |
| Ketoprofen | | | 0.30 | | | |
| Indomethacin | | | | 1.00 | | |
| Glycol salicylate | | | | | 1.00 | |
| Peppermint oil | | | | | | 0.10 |
| Purified water | as needed | as needed | as needed | as needed | as needed | as needed | adhesive article may be suitably designed according to the body of the body where the adhesive article is to be used. For instance, so that the adhesive article can be used on the face, it may be cut into the shape of a face, with suitable cut-outs for the eyes, nose, mouth, and chin.

Also, in the method for manufacturing the adhesive article, the backing may be applied to the adhesive layer after the release sheet has been coated with the adhesive base to form the adhesive layer.

The adhesive article of the present invention can be utilized for a medicinal or similar cataplasm, a cooling sheet, a cosmetic or similar compress, or the like.

EXAMPLES

Example 1

0.5 weight part UP-37K (trade name of Ina Food Industry; gel strength: 700 g/cm$^2$) as readily soluble agar, 3 weight parts polyacrylic acid, 0.5 weight part polyethylene glycol monostearate (trade name "MYS-10," made by Nikko Chemicals) as a surfactant, 0.3 weight part magnesium metasilicate aluminate, 0.3 weight part edetic acid, 0.2 weight part tartaric acid, 0.2 weight part methylparaben, 0.5 weight part crotamitone, and 1 weight part L-menthol were added to hot water. Next, a mixture composed of 5 weight parts sodium polyacrylate and 30 weight part glycerol was added under stirring, and purified water was added to bring the total amount up to 100 weight parts. This mixture was kneaded and stirred for 10 minutes at 70° C. to prepare an adhesive base.

Next, a polyester backing was coated with the adhesive base obtained above, so that the coating amount was 1000 g/cm$^2$. A release sheet was affixed to this to form an adhesive layer (thickness of approximately 1.40 mm). This product was then cut to a size of 14 cm×10 cm to obtain an adhesive article.

The adhesive article thus obtained was measured for the tack strength of the adhesive layer according to the rolling ball tack test of JIS Z 0237. These results are given in Table 2.

The shape retention of the adhesive layer was evaluated according to the following criteria. These results are given in Table 2 using the following symbols.

"◯": No adhesive was left on the finger when the surface of the adhesive layer was touched with a finger.

"Δ": Only a little adhesive was left on the finger when the surface of the adhesive layer was touched with a finger.

"x": A large amount of adhesive was left on the finger when the surface of the adhesive layer was touched with a finger.

The oozing of the adhesive layer was evaluated according to the following criteria. These results are given in Table 2 using the following symbols.

"◯": No oozing of adhesive into the backing was noted.

"Δ": Oozing of adhesive into the backing was noted.

"x": The adhesive oozed to the front side of the backing (the side where the adhesive layer is not laminated).

Extrusion of the adhesive layer was evaluated according to the following criteria. These results are given in Table 2 using the following symbols.

"◯": No extrusion of adhesive layer from adhesive article was noted.

"Δ": Part of the adhesive layer extruded from the ends of the adhesive article.

"x": The adhesive layer extruded all the way around the ends of the adhesive article.

The adhesive article was then applied to an upper arm, the sticky residue left behind after the adhesive article was peeled off an hour later was examined, and this was evaluated according to the following criteria. These results are given in Table 2 using the following symbols.

"○": No adhesive remained on the skin.

"Δ": Only a little adhesive remained on the skin.

"x": A large amount of adhesive remained on the skin.

The L-menthol in the adhesive layer was quantified, and the percentage of remaining L-menthol was calculated from the following equation. These results are given in Table 2.

Remaining proportion (%)=(measured amount of L-menthol in the adhesive layer)/(theoretical amount of L-menthol in the adhesive layer)×100

TABLE 2

|  | Example 1 | Example 2 | Example 3 | Example 4 | Example 5 |
|---|---|---|---|---|---|
| Dissolution temperature (° C.) | 70 | 70 | 70 | 70 | 70 |
| Dissolution time (minutes) | 10 | 10 | 10 | 10 | 10 |
| State of agar | dissolved | dissolved | dissolved | dissolved | dissolved |
| Water volatilization during manufacture | little | little | little | little | little |
| Shape retention | ○ | ○ | ○ | ○ | ○ |
| Oozing | ○ | ○ | ○ | ○ | ○ |
| Extrusion | ○ | ○ | ○ | ○ | ○ |
| Sticky residue | ○ | ○ | ○ | ○ | ○ |
| Tack strength (ball tack value; mm) | 30 | 35 | 25 | 30 | 38 |
| Proportion of L-menthol remaining (%) | 100 | 100 | 100 | 98 | 99 |

|  | Example 6 | Example 7 | Example 8 | Example 9 | Example 10 |
|---|---|---|---|---|---|
| Dissolution temperature (° C.) | 70 | 70 | 70 | 70 | 70 |
| Dissolution time (minutes) | 10 | 10 | 10 | 10 | 10 |
| State of agar | dissolved | dissolved | dissolved | dissolved | dissolved |
| Water volatilization during manufacture | little | little | little | little | little |
| Shape retention | ○ | ○ | ○ | ○ | ○ |
| Oozing | ○ | ○ | ○ | ○ | ○ |
| Extrusion | ○ | ○ | ○ | ○ | ○ |
| Sticky residue | ○ | ○ | ○ | ○ | ○ |
| Tack strength (ball tack value; mm) | 43 | 40 | 25 | 20 | 50 |
| Proportion of L-menthol remaining (%) | 97 | 98 | 100 | 98 | 98 |

Examples 2 to 6

Adhesive bases were prepared in the same manner as in Example 1, except that the components shown in Table 1 were used. When these adhesive bases were scooped out with a metal spatula and examined visually, it was found that the readily soluble agar had thoroughly dissolved. The pH of the adhesive base was approximately 5 to 5.4.

The adhesive bases thus obtained were used to obtain adhesive articles in the same manner as in Example 1. The adhesive articles thus obtained were evaluated in the same manner as in Example 1. These results are given in Table 2.

Examples 7 to 10

Adhesive bases were prepared in the same manner as in Example 1, except that the components shown in Table 3 were used. When these adhesive bases were scooped out with a metal spatula and examined visually, it was found that the readily soluble agar had thoroughly dissolved. The pH of the adhesive base was approximately 5 to 5.4.

The adhesive bases thus obtained were used to obtain adhesive articles in the same manner as in Example 1. The adhesive articles thus obtained were evaluated in the same manner as in Example 1. These results are given in Table 2.

TABLE 3

|  | Example 7 | Example 8 | Example 9 | Example 10 | Comparative Example 1 | Comparative Example 2 |
|---|---|---|---|---|---|---|
| Readily soluble agar (700 g/cm$^2$) | 1.00 |  |  |  |  |  |
| Readily soluble agar (600 g/cm$^2$) |  | 0.50 |  |  |  |  |
| Readily soluble agar (400 g/cm$^2$) |  |  | 0.50 |  |  |  |
| Readily soluble agar (1000 g/cm$^2$) |  |  |  | 0.50 |  |  |
| Ordinary agar |  |  |  |  |  | 0.50 |
| Sodium polyacrylate | 5.00 | 5.00 | 5.00 | 5.00 | 5.00 | 5.00 |
| Polyacrylic acid |  | 3.00 | 3.00 | 3.00 | 3.00 | 3.00 |
| Polyvinyl alcohol |  |  |  |  |  |  |
| Polyvinylpyrrolidone | 1.00 |  |  |  |  |  |
| Glycerol |  | 30.00 | 30.00 | 30.00 | 30.00 | 30.00 |
| Polyethylene glycol | 20.00 |  |  |  |  |  |
| Sorbitol | 10.00 |  |  |  |  |  |
| Surfactant | 0.20 | 0.50 | 0.50 | 0.50 | 0.50 | 0.50 |
| Titanium oxide |  |  |  |  |  |  |

TABLE 3-continued

|  | Example 7 | Example 8 | Example 9 | Example 10 | Comparative Example 1 | Comparative Example 2 |
|---|---|---|---|---|---|---|
| Synthetic aluminum silicate | 2.00 | | | | | |
| Magnesium metasilicate aluminate | 0.35 | 0.30 | 0.30 | 0.30 | 0.30 | 0.30 |
| Edetic acid | 0.30 | 0.30 | 0.30 | 0.30 | 0.30 | 0.30 |
| Tartaric acid | 0.15 | 0.20 | 0.20 | 0.20 | 0.20 | 0.20 |
| Methylparaben | 0.20 | 0.20 | 0.20 | 0.20 | 0.20 | 0.20 |
| Crotamitone | 0.50 | 0.50 | 0.50 | 0.50 | 0.50 | 0.50 |
| Menthol | 1.00 | 1.00 | 1.00 | 1.00 | 1.00 | 1.00 |
| Camphor | | | | | | |
| Isopropanol | | | | | | |
| Ketoprofen | | | | | | |
| Indomethacin | | | | | | |
| Glycol salicylate | | | | | | |
| Peppermint oil | | | | | | |
| Purified water | as needed | as needed | as needed | as needed | as needed | as needed |

Comparative Example 1

An adhesive article was obtained in the same manner as in Example 1, except that, as shown in Table 3, a composition containing no agar was used, and the adhesive base was prepared by kneading and stirring the liquid mixture for 10 minutes at 70° C.

The adhesive base thus obtained was evaluated in the same manner as in Example 1. These results are given in Table 4.

TABLE 4

|  | Comparative Example 1 | Comparative Example 2 | Comparative Example 3 | Comparative Example 4 | Comparative Example 5 |
|---|---|---|---|---|---|
| Dissolution temperature (° C.) | 70 | 80 | 80 | 90 | 90 |
| Dissolution time (minutes) | 10 | 10 | 20 | 10 | 20 |
| State of agar | — | did not dissolve | partially dissolved | partially dissolved | dissolved |
| Water volatilization during manufacture | little | much | much | much | extremely much |
| Shape retention | X | X | Δ | Δ | ○ |
| Oozing | X | X | X | X | ○ |
| Extrusion | could not be evaluated | could not be evaluated | X | X | ○ |
| Sticky residue | could not be evaluated | could not be evaluated | Δ | Δ | Δ |
| Tack strength (ball tack value; mm) | could not be evaluated | could not be evaluated | 30 | 30 | 30 |
| Proportion of L-menthol remaining (%) | 100 | 95 | 90 | 85 | 80 |

Comparative Example 2

An adhesive article was obtained in the same manner as in Example 1, except that ordinary agar "S-7" (trade name of Ina Food Industry; gel strength 730 g/cm$^2$) was used instead of using "UP-37K" as readily soluble agar, and that the adhesive base was prepared by kneading and stirring the liquid mixture for 10 minutes at 80° C. The agar was in an undissolved state in the obtained adhesive base.

The adhesive article thus obtained was evaluated in the same manner as in Example 1, the results of which are given in Table 4.

Comparative Example 3

An adhesive article was obtained in the same manner as in Comparative Example 2, except that the adhesive base was prepared by kneading and stirring the liquid mixture for 20 minutes at 80° C. Part of the agar was in an undissolved state in the obtained adhesive base.

The adhesive article thus obtained was evaluated in the same manner as in Example 1, the results of which are given in Table 4.

Comparative Example 4

An adhesive article was obtained in the same manner as in Comparative Example 2, except that the adhesive base was prepared by kneading and stirring the liquid mixture for 10 minutes at 90° C. Part of the agar was in an undissolved state in the obtained adhesive base.

The adhesive article thus obtained was evaluated in the same manner as in Example 1, the results of which are given in Table 4.

Comparative Example 5

An adhesive article was obtained in the same manner as in Comparative Example 2, except that the adhesive base was prepared by kneading and stirring the liquid mixture for 20 minutes at 90° C. It was confirmed that the agar was thoroughly dissolved in the obtained adhesive base.

The adhesive article thus obtained was evaluated in the same manner as in Example 1, the results of which are given in Table 4.

As shown in Table 2, it was confirmed that the adhesive articles of Examples 1 to 10 had excellent shape retention and sufficient tack strength, and that sticky residue was sufficiently reduced. It was also confirmed that the adhesive articles contained enough water and that the added L-menthol adequately remained in the adhesive layer.

Example 11

1.0 weight part synthetic aluminum silicate was dispersed in 79.95 weight parts purified water. 1.0 weight part polyvinylpyrrolidone was added to this, and then 0.25 weight part sodium edetate and a mixture of 3.0 weight part polyethylene glycol and 0.4 weight part readily soluble agar (trade name "UP-37K," made by Ina Food Industry; gel strength 700 g/cm$^2$) were added. A mixture of 7.0 weight parts sodium polyacrylate, 0.3 weight part magnesium metasilicate aluminate, and 7.0 weight parts polyethylene glycol was then further added, and the system was stirred until it became a uniform solution. After this, 0.1 weight part tartaric acid was added to the solution, which was further stirred to prepare an adhesive base. Table 5 shows the various components and their blend proportions in the adhesive base thus prepared. The numerical values in Table 5 indicate weight percentages. The pH of the adhesive base was 6.4.

TABLE 5

| | Example 11 | Example 12 | Example 13 | Example 14 |
|---|---|---|---|---|
| Gelatin | — | — | — | — |
| Polyacrylic acid | — | — | 0.5 | — |
| Sodium polyacrylate | 7.0 | 3.0 | 6.0 | 3.0 |
| Xanthan gum | — | — | — | 0.5 |
| Polyvinylpyrrolidone | 1.0 | 0.5 | 0.1 | — |
| Readily soluble agar | 0.4 | 0.5 | 0.7 | 0.5 |
| Synthetic aluminum silicate | 1.0 | 1.5 | 3.0 | 1.5 |
| Polyethylene glycol | 10.0 | 12.0 | 8.0 | 8.0 |
| Glycerol | — | — | — | 2.0 |
| Magnesium metasilicate aluminate | 0.30 | 0.35 | 0.45 | — |
| Magnesium silicate aluminate | — | — | — | — |
| Dry magnesium aluminate | — | — | — | 0.20 |
| Sodium edetate | 0.25 | 0.35 | 0.40 | 0.20 |
| Lactic acid | — | 0.10 | — | — |
| Tartaric acid | 0.10 | — | 0.10 | 0.10 |
| Purified water | 79.95 | 81.70 | 80.75 | 84.00 |
| Evaluation | | | | |
| Oozing from ointment | no | no | no | no |
| Adhesion (mm) | 25.2 | 28.8 | 51.5 | 39.8 |
| Usage feel | ○ | ○ | ○ | ○ |
| Lead time (days) | 9 | 10 | 11 | 8 |

Next, the adhesive base was spread out in a thickness of 1.4 mm over a piece of cloth (25 cm×25 cm) as a backing made by Japan Vilene, thereby forming a coating film. A release film was affixed over this coating, and this product was stored at room temperature to form an adhesive layer. This gave an adhesive article that could be shipped as a finished product. The criterion for determining whether the adhesive article could be shipped was as follows.

It was determined that shipping was possible at the point when the gel strength of the adhesive layer stabilized over time. The number of days from the start of the preparation of the adhesive base until the point when shipping was possible (lead time) is shown in Table 5.

The adhesive article thus obtained was measured for the tack strength of the adhesive layer according to the rolling ball tack test of JIS Z 0237. These results are given in Table 5.

The oozing of water from the adhesive layer of the obtained adhesive article was evaluated according to the following criteria. These results are given in Table 5.

"no": No discoloration of the backing cross, or oozing of water to the backing cross side was seen.

"yes": Discoloration of the backing cross, or oozing of water to the backing cross side was seen.

If there was any problem with the usage feel (moistness, stickiness) in applying the obtained adhesive article to the face, it was noted in Table 5. If there were no particular problems, this was indicated with a "○" symbol.

Examples 12 to 14

Adhesive bases were obtained in the same manner as in Example 11, except that the compositions shown in Table 5 were used in the preparation of the adhesive base. The pH of the adhesive base was 6.3 to 6.5.

The adhesive bases thus obtained were used to obtain adhesive articles in the same manner as in Example 11. The number of days from the start of the preparation of the adhesive base until the point when shipping was possible (lead time) is shown in Table 5. Further, the adhesive article thus obtained was evaluated in the same manner as in Example 11, the results of which are given in Table 5.

Comparative Examples 6 to 8

Adhesive articles were obtained in the same manner as in Example 11, except that gelatin and the compositions shown in Table 6 were used in the preparation of the adhesive base.

TABLE 6

| | Comparative Example 6 | Comparative Example 7 | Comparative Example 8 | Example 15 | Example 16 | Example 17 |
|---|---|---|---|---|---|---|
| Gelatin | 1.0 | 1.2 | 1.0 | — | — | — |
| Polyacrylic acid | — | — | — | — | 1.5 | — |
| Sodium polyacrylate | 6.0 | 3.0 | 9.0 | 7.0 | 4.0 | 10.0 |
| Xanthan gum | — | — | 0.5 | — | — | — |
| Polyvinylpyrrolidone | — | — | — | 1.5 | — | — |
| Readily soluble agar | — | — | 0.5 | 0.4 | 1.0 | 1.0 |
| Synthetic aluminum silicate | 4.0 | 5.0 | 4.0 | 1.0 | 3.0 4.0 | |
| Polyethylene glycol | 8.0 | — | 10.0 | 10.0 | 8.0 | 6.0 |
| Glycerol | — | 8.0 | 5.0 | — | — | 4.0 |
| Magnesium metasilicate aluminate | — | — | — | 0.30 | — | — |
| Magnesium silicate aluminate | — | — | 0.6 | — | — | 0.6 |
| Dry magnesium aluminate | 0.25 | 0.70 | — | — | 0.30 | — |

TABLE 6-continued

|  | Comparative Example 6 | Comparative Example 7 | Comparative Example 8 | Example 15 | Example 16 | Example 17 |
| --- | --- | --- | --- | --- | --- | --- |
| Sodium edetate | 0.40 | 0.45 | 0.35 | 0.25 | 0.30 | 0.20 |
| Lactic acid | 0.10 | — | — | — | 0.10 | 0.10 |
| Tartaric acid | — | 0.10 | 0.10 | 0.10 | — | — |
| Sorbitol | — | — | — | — | 10.0 | 5.0 |
| Purified water | 80.25 | 81.55 | 68.95 | 79.45 | 71.80 | 69.10 |
| Evaluation |  |  |  |  |  |  |
| Oozing from ointment | yes | yes | yes | no | no | no |
| Adhesion (mm) | — | — | — | 20.5 | 61.1 | 58.2 |
| Usage feel | ○ | ○ | ○ | sticky | ○ | not very moist |
| Lead time (days) | — | — | — | 14 | 14 | 16 |

The adhesive articles thus obtained were evaluated in the same manner as in Example 11, the results of which are given in Table 6. The adhesion and lead time could not be measured for the adhesive articles of Comparative Examples 6 to 8 because water oozed from the adhesive layer.

Examples 15 to 17

Adhesive articles were obtained in the same manner as in Example 11, except that the compositions shown in Table 6 were used in the preparation of the adhesive base.

The adhesive articles thus obtained were evaluated in the same manner as in Example 11, the results of which are given in Table 6.

As shown in Table 5, it was confirmed that the adhesive articles of Examples 11 to 14 had excellent usage feel, had sufficiently reduced oozing of water from the ointment, and had adequate tack strength. On the other hand, water oozed from the ointment with the adhesive articles of Comparative Examples 6 to 8, in which gelatin was used. A comparison of the adhesive articles of Examples 15 to 17 with the adhesive articles of Examples 11 to 14 reveals that the former had inferior usage feel or tack strength.

Furthermore, the adhesive articles of Examples 11 to 14 had a lead time of 8 to 11 days, while the adhesive articles of Examples 15 to 17 had a lead time of 14 to 16 days. It can be seen from this that the adhesive articles of Examples 11 to 14 were better in terms of productivity.

INDUSTRIAL APPLICABILITY

The present invention provides an adhesive article that has a sufficiently high water content, excellent tack strength, and sufficiently reduced sticky residue, even when the blend is such that the desired components are contained and the desired pH is achieved.

The invention claimed is:

1. An adhesive article, comprising:
   a backing; and
   an adhesive layer disposed on at least one side of the backing, the adhesive layer being formed from an adhesive base which comprises readily soluble agar that dissolves 100% at a temperature of 70° C.,
   wherein the adhesive base does not comprise gelatin.

2. The adhesive article according to claim 1, wherein the adhesive base further contains a volatile component or a pyrolyzable component.

3. The adhesive article according to claim 1, wherein the adhesive base further contains a polyacrylic acid and/or a salt thereof.

4. The adhesive article according to claim 1, wherein the adhesive base further contains a polyvinyl alcohol.

5. The adhesive article according to claim 1, wherein the adhesive base further contains a polyvinylpyrrolidone or xanthan gum.

6. The adhesive article according to claim 1, wherein the readily soluble agar has a gel strength of from 450 to 1000 g/cm2.

7. The adhesive article according to claim 1, wherein said adhesive article is a water-based adhesive article.

8. The adhesive article according to claim 1, wherein the adhesive base further comprises a water-soluble polymer in an amount of 3.0 to 10 wt %, and xanthan gum and/or a polyvinylpyrrolidone in a combined amount of from 0.01 to 1.4 wt %.

* * * * *